United States Patent
Dority et al.

[11] Patent Number: 5,908,418
[45] Date of Patent: Jun. 1, 1999

[54] HAND HELD COAGULATING DEVICE

[76] Inventors: Douglas B. Dority, 25 Castlerock Dr., Mill Valley, Calif. 94941; Morton J. Jensen, 1424 Polk St. #52, San Francisco, Calif. 94109

[21] Appl. No.: 08/713,737

[22] Filed: Sep. 13, 1996

[51] Int. Cl.⁶ .................................................. A61B 17/36
[52] U.S. Cl. ................................. 606/40; 606/13; 607/93
[58] Field of Search ........................... 606/40, 41, 42, 606/34, 37, 38, 49, 1, 3, 7, 13, 9, 16, 17, 18, 2; 607/88, 90, 93; 219/85.12

[56] References Cited

U.S. PATENT DOCUMENTS

| | | |
|---|---|---|
| 3,234,356 | 2/1966 | Babb . |
| 3,299,884 | 1/1967 | Moore et al. ............................ 607/93 |
| 3,527,932 | 9/1970 | Thomas .................................. 607/90 |
| 3,547,125 | 12/1970 | Tagnon . |
| 3,723,704 | 3/1973 | Silverthorne . |
| 3,864,547 | 2/1975 | Ray ..................................... 219/85.12 |
| 4,108,181 | 8/1978 | Saliaris . |
| 4,126,136 | 11/1978 | Auth et al. . |
| 4,233,493 | 11/1980 | Nath . |
| 4,539,987 | 9/1985 | Nath et al. . |
| 4,671,349 | 6/1987 | Wolk ................................... 165/104.26 |
| 4,753,154 | 6/1988 | Higashi ............................... 165/104.26 |
| 4,884,568 | 12/1989 | Hahn . |
| 5,001,608 | 3/1991 | Kehrli et al. ............................. 607/90 |
| 5,010,452 | 4/1991 | Krebser et al. ........................... 607/90 |
| 5,125,923 | 6/1992 | Tanner et al. . |
| 5,292,346 | 3/1994 | Ceravolo . |
| 5,344,418 | 9/1994 | Ghaffari ..................................... 606/9 |
| 5,376,087 | 12/1994 | Haber et al. . |
| 5,401,273 | 3/1995 | Shippert . |
| 5,464,436 | 11/1995 | Smith . |
| 5,520,684 | 5/1996 | Imran ..................................... 606/41 |
| 5,553,629 | 9/1996 | Keipert et al. ............................ 606/16 |
| 5,647,429 | 7/1997 | Oktay et al. ....................... 165/104.26 |
| 5,725,049 | 3/1998 | Swanson et al. .................. 165/104.26 |

FOREIGN PATENT DOCUMENTS 1564435 1/1976 United Kingdom .

*Primary Examiner*—Richard J. Apley
*Assistant Examiner*—Justine R. Yu
*Attorney, Agent, or Firm*—Burns, Doane, Swecker & Mathis, L.L.P.

[57] ABSTRACT

A hand held coagulating device exhibiting superior radiation transfer characteristics and providing a cooled handle for improved user comfort. An exemplary embodiment includes an outer shell housing internal components of the device and providing a surface at which a user of the device can hold the device during a surgical procedure. A contact element positioned in an opening in a forward end of the shell is placed against an area of tissue or blood to be coagulated, and radiation produced by a radiation source, such as an incandescent lamp, is transmitted through the contact element to the tissue or blood for an appropriate period of time. In one embodiment, a curved reflector is disposed near the radiation source to direct the radiation toward the contact element, and a conical collector is situated between the radiation source and the contact element to focus the radiation through the contact element. In another embodiment, a heat sink is positioned in an opening in an aft end of the shell for conducting heat to the surrounding environment. An adiabatic heat pipe is connected between the radiation source and the heat sink so that heat is transferred directly from the radiation source to the outside air while the surface used for holding the device remains cool.

12 Claims, 2 Drawing Sheets

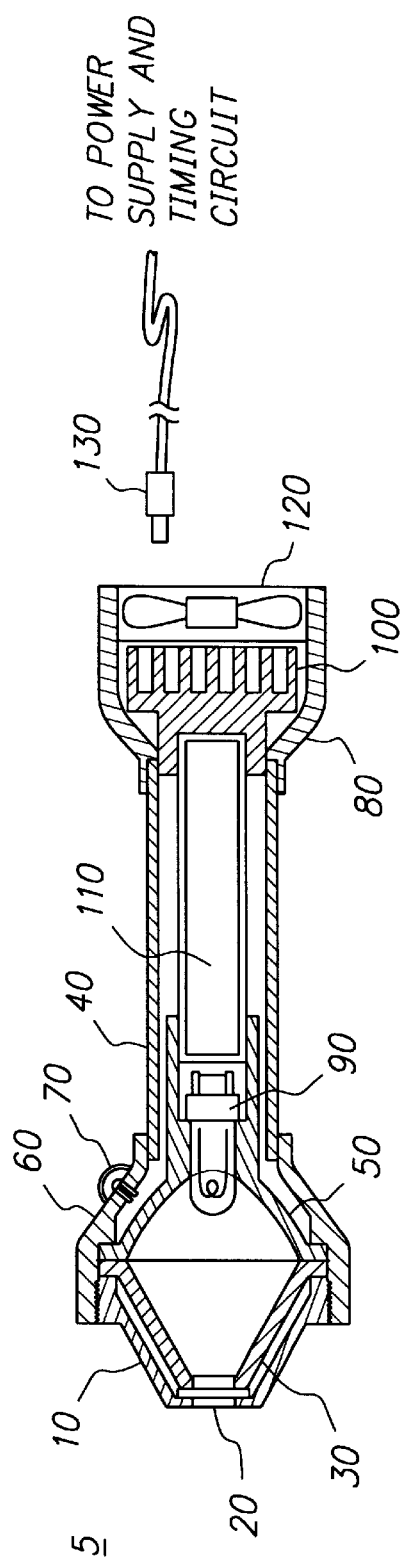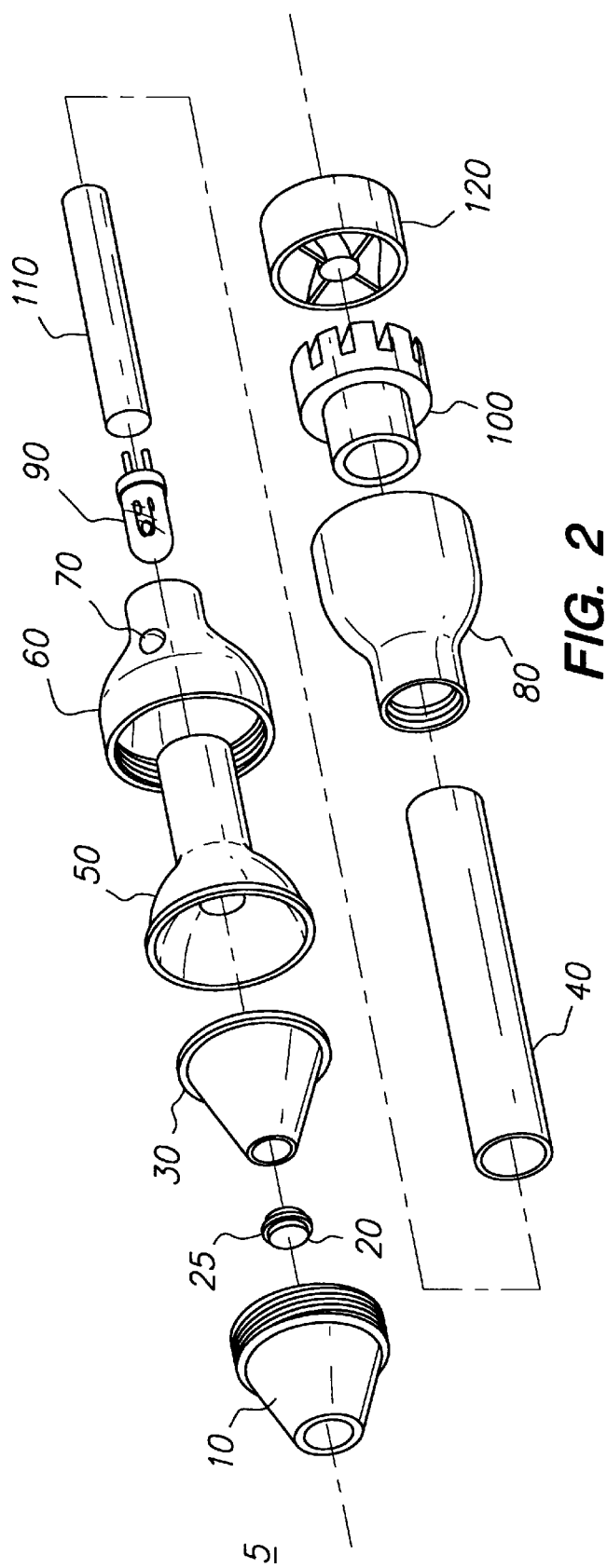

HAND HELD COAGULATING DEVICE

FIELD OF THE INVENTION

The present invention relates to coagulating devices used, for example, during surgical procedures, and more particularly to hand held coagulating devices employing radiation to coagulate blood or tissue.

BACKGROUND OF THE INVENTION

Medical treatments today often require that areas of organic tissue be cauterized or coagulated quickly, efficiently, and safely during the course of a surgical procedure. For example, surface tissue on a highly vascularized organ such as the human liver may be cauterized immediately following the making of a surgical incision in order to prevent excessive bleeding. Alternatively, retinal tissue in a human eye may be photocoagulated during opthalmic surgery to correct injury, or skin tissue on a human scalp may be coagulated during hair transplant surgery to prevent bleeding resulting from graft incisions. Many prior art devices have been developed to perform cauterization or coagulation as appropriate for such varied applications. Known devices range from simple direct-contact cauteries, employing a heated wire element to burn or sear relatively large areas of tissue, to more complex laser photocoagulators using highly coherent, monochromatic laser light to perform pin-point coagulation of delicate tissue.

One particular class of coagulator, of primary interest in the present application, includes devices employing noncoherent, broadband radiation, such as that produced by an incandescent light source, to achieve tissue coagulation. Such devices are extremely beneficial in that noncoherent radiation can be used effectively to coagulate tissue or blood in a wide variety of surgical applications. However, physical limitations associated with known devices in this class tend to limit their practical usefulness.

For example, because the intense heat generated by an incandescent light source can create discomfort, or even danger, for a user of such a device, typical prior art devices are configured to physically isolate a user's hand from the light source. See, for example, U.S. Pat. No. 4,233,493 and U.S. Pat. No. 4,884,568. Such devices tend to be bulky, and therefore awkward, from the perspective of a user attempting to perform a precise or lengthy surgical procedure. Other prior art devices rely on a combination of short-duration coagulation pulses and thick, heat sinking contact elements positioned between the light source and the tissue being coagulated to prevent over-heating. See, for example, U.S. Pat. No. 5,539,987. While such devices are more compact, the limitations imposed in order to prevent over-heating render these devices ineffective for many applications.

Additionally, each of the above cited prior art devices provides less than optimal efficiency in terms of transferring radiation from the light source to the tissue being coagulated. As a result, relatively high power levels must be used to achieve coagulation in a given context. This not only results in undue power consumption, but also adds to the over-heating problem just described. Thus, there is a need for a coagulating device providing improved radiation transfer characteristics and enabling a user to comfortably hold and manipulate the device during a surgical procedure.

SUMMARY OF THE INVENTION

The present invention fulfills the above-described and other needs by providing a streamlined, hand held coagulating device exhibiting superior radiation transfer characteristics and providing a cooled handle for improved user comfort. An exemplary embodiment of the present invention includes an outer shell for housing internal components of the coagulating device and for providing a surface at which a user of the device can conveniently and comfortably hold the device during a surgical procedure. A radiation source disposed within the shell generates the radiation used to achieve coagulation. Additionally, a contact element constructed of, for example, sapphire or Teflon is positioned in an opening in a forward end of the shell. During a surgical procedure, the contact element is placed against an area of tissue or blood which is to be coagulated, and the radiation produced by the radiation source is transmitted through the contact element to the tissue or blood for an appropriate period of time.

In one embodiment, a curved reflector is disposed within the shell near the radiation source in order to direct the noncoherent radiation generated by the light source toward the contact element. Also, a conical collector is situated between the light source and the contact element for focusing the radiation through the contact element. The combination of the curved reflector and the conical collector provides a highly efficient transfer of coagulating radiation from the light source to the area of blood or tissue to be coagulated.

In another embodiment, a heat sink is positioned in an opening in an aft end of the shell for conducting the often intense heat generated by the radiation source to the outside environment. An adiabatic heat pipe is connected between the radiation source and the heat sink so that the heat is efficiently transferred directly from its source to the surrounding air. By transferring heat in this way, a region of the outer surface of the shell is kept cool so that a user of the device can comfortably hold and manipulate the device throughout a surgical procedure.

These and other features of the present invention are explained hereinafter with reference to an illustrative embodiment depicted in the accompanying drawings. Those skilled in the art will appreciate that the depicted embodiment is provided for purposes of explanation only and that numerous additional embodiments combining various aspects of the present invention are contemplated herein.

BRIEF DESCRIPTION OF THE DRAWINGS

FIG. 1 is a cross-sectional side view of an exemplary embodiment of a blood coagulating device constructed in accordance with the teachings of the present invention.

FIG. 2 is an exploded perspective view of the exemplary embodiment of FIG. 1.

DETAILED DESCRIPTION OF THE PREFERRED EMBODIMENTS

Figure 3:
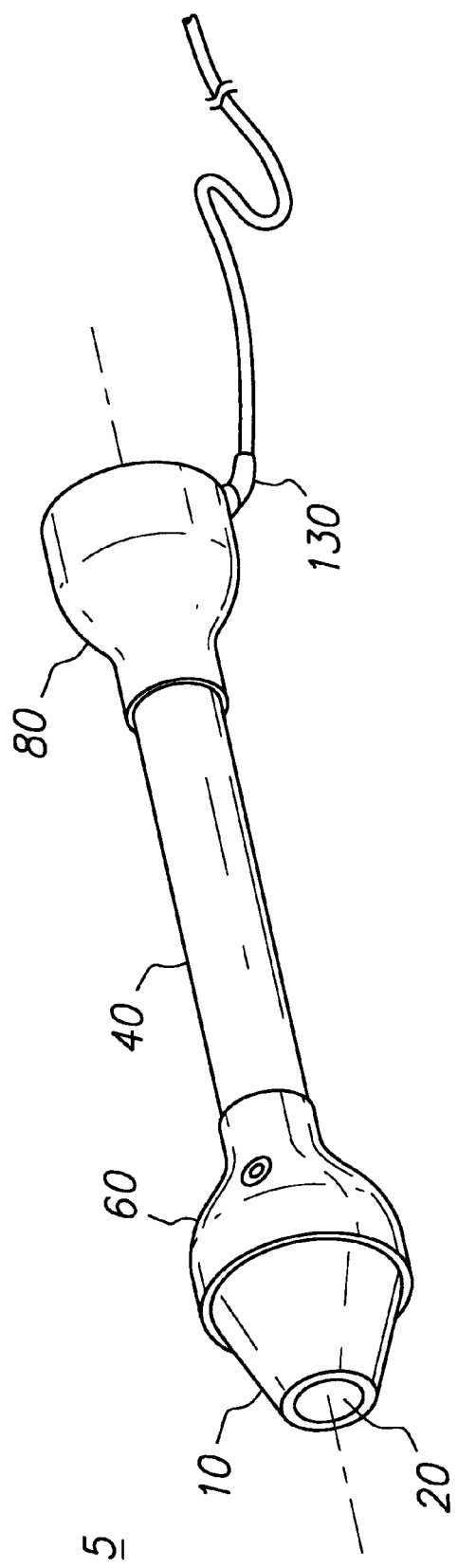
FIG. 3 is a perspective view of the exemplary embodiment of FIG. 1 in an assembled configuration.

FIGS. 1–3 depict an exemplary embodiment of a hand held blood coagulating device 5 constructed in accordance with the teachings of the present invention. As shown in FIG. 1, a forward cone 10 is connected to a forward hood 60 which is in turn connected to an elongated body 40. The elongated body 40 is in turn connected to a rear hood 80. The forward cone 10, the forward hood 60, the elongated body 40, and the rear hood 80, may be constructed, for example, of aluminum, and together form an outer shell for housing internal components of the coagulating device 5. The elongated body 40 also provides an outer surface area, or handle, at which a user of the device may hold and manipulate the device during a surgical procedure.

As shown, a tissue contact element 20, constructed for example of Teflon or sapphire, is positioned in an opening in a leading surface of the forward cone 10. A conical collector 30 and an abutting curved reflector 50, constructed for example of aluminum, are positioned within the outer shell in a cavity formed by the forward cone 10 and the forward hood 60. As shown, the conical collector 30 is positioned such that an outer contour of the conical collector 30 roughly parallels an inner contour of the forward cone 10. Additionally, the curved reflector 50 is positioned such that an outer contour of the collector 50 roughly parallels an inner contour of the forward hood 60. In each case an air gap is provided for purposes of heat insulation. A forward edge of the conical collector 30 is used to hold the tissue contact element 20 in place by means of an O-ring 25.

As shown, a radiation source 90, such as an incandescent tungsten-halogen lamp, is positioned within an inner slot of the curved reflector 50 such that the radiation source 90 is positioned within the outer shell proximate the point of contact between the forward hood 60 and the elongated body 40. As a result, the radiation source 90 is positioned within a cavity formed by the inner surfaces of the conical collector 30 and the curved reflector 50. The inner surfaces of the conical collector 30 and the curved reflector 50 are light reflecting and may be gold plated for improved reflectivity.

A heat sink 100 and an electric fan 120 are positioned adjacent one another within the outer shell in a cavity formed by the rear hood 80. Also, an adiabatic heat pipe 110 is positioned within the outer shell in a cavity formed by the elongated body 40. The heat pipe 110 may be of the type manufactured by Thermacore, Inc., 780 Eden Road, Lancaster, Pa. 17601. As shown, one end of the heat pipe 110 is connected to the base of the radiation source 90 and to an aft portion of the curved reflector 50. An opposite end of the heat pipe 110 is connected to the heat sink 100.

An electrical connector 130, when connected to a socket (not shown) in the side of the rear hood 80, is used to electrically couple the radiation source 90 and the electric fan 120 to an external power supply and timing control circuit (not shown). The electrical connections are made switchable by means of an electric switch 70 positioned in a slot in the forward hood 60. The electric switch 70 may be hermetically sealed by a rubberized protective cover, as is well known in the art.

FIG. 2 is an exploded perspective view of the coagulating device 5 of FIG. 1 depicting each component described with reference to FIG. 1 in its respective order of assembly. FIG. 3 is a perspective view of the coagulating device 5 of FIGS. 1 and 2 as it is assembled.

In operation, a user of the device 5, holding the device in one hand as if it were a pen, applies the tissue contact element 20 to an area of tissue or blood to be coagulated. As described above, the tissue element 20 is constructed of an appropriate material such that the tissue contact element 20 will transmit radiation generated by the light source 90, but will not stick to the area of tissue or blood being coagulated. By means of the switch 70, the user supplies power to the radiation source 90. As described above, the radiation source 90 can be an incandescent lamp emitting broadband, non-coherent radiation. The inner light reflecting surface of the curved reflector 50 reflects the radiation generated by the source 90 toward the tissue contact element 20. The inner light reflecting surface of the conical collector 30 reflects radiation generated by the source 90, and reflected by the curved reflector 50, to focus the radiation through the tissue contact element 20 and to the tissue or blood being coagulated. As is well known in the art, applying broadband radiation to an area of tissue or blood in this way is an effective means of achieving coagulation. The intensity of the radiation source 90, as well as the precise duration of the radiation pulses applied to the blood or tissue, are set by means of controls (not shown) at the external timing control circuit and will vary from application to application.

The heat pipe 110 is used to dissipate the intense heat generated by the radiation source 90 in such a way that the outer surface of the body 40 and the forward hood 60 will remain cool enough that the user can comfortably hold the device throughout a surgical procedure. Operation of the heat pipe 110 is known in the art. Briefly, heat is dissipated by cyclicly evaporating and condensing working fluid within the heat pipe. The working fluid is evaporated at an evaporator end of the heat pipe 110, which is connected to the radiation source 90 and the curved reflector 50. The vaporized working fluid travels the length of the heat pipe by means of a pressure gradient created by the evaporation process. Heat is then drawn from the heat pipe 110 by the heat sink 100 and the electric fan 120 which are connected to a condenser end of the heat pipe 110. Upon reaching the condenser end of the heat pipe 110, the vaporized working fluid condenses and releases its latent heat of vaporization. The condensed working fluid is then drawn into a porous wick within the heat pipe 110 where it is returned to the evaporator end of the heat pipe 110 by means of capillary action within the wick. Continual evaporation and condensation of the working fluid enables heat to be adiabatically transferred from one end of the heat pipe 110 to the other. Thus, heat generated within the coagulating device 5 is transferred from its source 90 to the surrounding environment without creating danger or discomfort for the user.

In addition to permitting the construction of a compact, hand held coagulating device which is simultaneously powerful, safe, and comfortable for the user, such strategic use of the heat pipe 110 also permits construction of a coagulating device which is more efficient in transferring radiation from its source to a target as compared to prior art devices. This results from the fact that the radiation source 90 can be positioned at a forward end of the device, close to the target tissue. Also, because the tissue contact element 20 need not be used to dissipate heat, it may be made as thin as is necessary for a given application. Furthermore, the focusing effect of the conical collector 30, which is not disclosed in the prior art devices, maximizes the transmission of radiation through the contact element 20 irrespective of the heat pipe 110. By efficiently transferring radiation from its source to the target tissue, a device constructed in accordance with the teachings of the present invention is capable of coagulating tissue using lower radiation source power levels as compared to the prior art devices. In addition to cost savings, such reduced power consumption also minimizes the over-heating problem described above.

In sum, the present invention provides a compact, convenient, and highly efficient hand held coagulating device. Such a device can be used to coagulate tissue or blood in a wide variety of applications. The streamlined construction and cooled outer surface of the device enables a user to easily perform precise, repetitive operations over long periods of time without fatigue and without discomfort due to overheating.

It will be appreciated that the present invention is not limited to the specific embodiment which has been described herein in order to facilitate an understanding of the underlying principles of the invention. For example, the novel teaching of providing a conical collector in a coagulating device to focus radiation through a tissue contact element can be applied independent of the also novel teaching of employing an adiabatic heat pump, or pipe, in a coagulating device to remedy the problems of overheating associated with the prior art devices. The scope of the invention, therefore, is defined by the claims which are appended hereto, rather than the foregoing description, and all equivalents which are consistent with the meaning of the claims are intended to be embraced therein.

We claim:

1. A blood coagulating device, comprising:

a shell for housing components of the coagulating device and for providing an outer surface at which the coagulating device can be held in hand by a user of the coagulating device during a surgical procedure;

a radiation source disposed within said shell for generating radiation used to coagulate blood or tissue during the surgical procedure;

a contact element positioned in an opening in a forward end of said shell for transmitting the radiation generated by said radiation source to an area of tissue or blood to be coagulated;

a curved reflector disposed within said shell proximate said radiation source for directing the radiation generated by said radiation source toward said contact element;

a conical collector disposed within said shell between said radiation source and said contact element for focusing the radiation generated by said radiation source through said contact element;

a heat sink positioned in an opening in a proximal end of said shell for conducting heat generated by said radiation source to an outside environment surrounding said shell; and an adiabatic heat pipe having an evaporator end connected to said radiation source and a condenser end connected to said heat sink for transferring heat from said radiation source to said heat sink and for keeping a region of the outer surface of said shell cool enough that the user can comfortably hold the coagulator in hand during the surgical procedure.

2. A blood coagulating device as in claim 1, further comprising a fan positioned in the opening in the proximal end of said shell adjacent said heat sink for aiding in the removal of heat from the coagulating device to the surrounding environment.

3. A blood coagulating device as in claim 1, further comprising means for electrically coupling said radiation source to an external power supply and an external timing control circuit.

4. A blood coagulating device as in claim 1, further comprising a switch for enabling the user of the coagulating device to apply power from an external power supply to said radiation source.

5. A blood coagulating device as in claim 1, wherein said shell, said curved reflector, and said conical collector are constructed of aluminum.

6. A blood coagulating device as in claim 1, wherein said curved reflector and said conical collector are gold plated.

7. A blood coagulating device as in claim 1, wherein said radiation source is an incandescent lamp.

8. A blood coagulating device as in claim 1, wherein said shell comprises a forward cone, a forward hood, a cylindrical body, and a rear hood assembled to enclose said radiation source, said curved reflector, said conical collector, said heat sink, and said heat pipe.

9. A blood coagulating device as in claim 1, wherein said contact element is constructed of a Teflon material.

10. A blood coagulating device as in claim 1, wherein said contact element is constructed of sapphire.

11. A blood coagulating device as in claim 1, wherein a light reflecting surface of said curved reflector forms a paraboloid and wherein said radiation source is positioned at a focal point of the paraboloid.

12. A method of coagulating blood or tissue during surgery comprising the steps of:

providing a coagulating device including a distal end with a radiation source, a heat sink positioned at a proximal end of the coagulating device for conducting heat generated by the radiation source to an outside environment surrounding the coagulating device, an adiabatic heat pipe transferring heat from the radiation source to the heat sink, wherein the adiabatic heat pipe transfers heat by evaporation and condensation of a working fluid within the heat pipe, and a conical collector for focusing radiation generated by the radiation source through a contact element of the blood coagulation device; and applying the contact element to an area of tissue for blood to be coagulated.

* * * * *